United States Patent [19]

Lafargue et al.

[11] Patent Number: 6,048,497
[45] Date of Patent: Apr. 11, 2000

[54] METHOD FOR EVALUATING A POLLUTION CHARACTERISTIC OF A SOIL SAMPLE

[75] Inventors: Eric Lafargue, Carrieres sur Seine; Jean Ducreux, Bougival; François Marquis, Montlignon; Daniel Pillot, Paris, all of France

[73] Assignee: Institut Francais du Petrole, France

[21] Appl. No.: 09/114,947

[22] Filed: Jul. 14, 1998

Related U.S. Application Data

[62] Division of application No. 08/747,758, Nov. 13, 1996, Pat. No. 5,786,225.

[30] Foreign Application Priority Data

Sep. 12, 1996 [FR] France .................................. 96 11582

[51] Int. Cl.[7] .................................................. G01N 31/12
[52] U.S. Cl. .......................... 422/80; 422/78; 422/82.05; 422/93
[58] Field of Search .................. 436/25, 28, 29, 436/30, 31, 32, 139, 140, 141, 143, 145, 146, 147, 149, 150, 154, 155, 157, 158; 422/54, 78, 80, 82.05, 93

[56] References Cited

U.S. PATENT DOCUMENTS

| | | | |
|---|---|---|---|
| 3,953,171 | 4/1976 | Espitalie et al. | 422/80 |
| 4,153,415 | 5/1979 | Espitalie et al. | 422/80 |
| 4,213,763 | 7/1980 | Madec et al. | 422/80 |
| 4,229,181 | 10/1980 | Espitalie et al. | 422/78 |
| 4,352,673 | 10/1982 | Espitalie et al. | 422/80 |
| 4,519,983 | 5/1985 | Espitalie et al. | 422/80 |
| 4,837,158 | 6/1989 | Toulhoat et al. | 436/37 |
| 5,786,225 | 7/1998 | LaFarque et al. | 422/82.05 |
| 5,811,308 | 9/1998 | Espitalie et al. | 436/145 |

Primary Examiner—Randy Gulakowski
Assistant Examiner—Alexander Markoff
Attorney, Agent, or Firm—Millen, White, Zelano & Branigan

[57] ABSTRACT

A device for evaluating at least one pollution characteristic of natural soils contaminated by hydrocarbon compounds, said device comprising a first heater heating said sample in a non-oxidizing atmosphere, a measuring device determining an amount of hydrocarbon compounds released after feeding the sample into said first heater, a sample transfer device transferring the sample from the first heater into a second heater operating in an oxidizing atmosphere, a $CO_2$ measuring device determining $CO_2$ contained each effluent discharged from the two heaters, said $CO_2$ measuring device measuring continuously the $CO_2$ throughout the heating cycle of the first and the second heaters and including a device measuring CO contained in each effluent discharged from the two heaters, a temperature controller controlling the temperature of samples waiting to be fed into said heating means, and a device determining the pollution characteristic.

7 Claims, 3 Drawing Sheets

METHOD FOR EVALUATING A POLLUTION CHARACTERISTIC OF A SOIL SAMPLE

This application is a divisional application of Ser. No. 08/747,758, filed Nov. 13, 1996, now U.S. Pat. No. 5,786,225.

FIELD OF THE INVENTION

The present invention relates to a method and to a device for determining at least one pollution characteristic of a natural soil potentially or really contaminated by pollutants, notably hydrocarbons and/or derivatives.

BACKGROUND OF THE INVENTION

With a view to a better understanding, it should be reminded that:

during an accidental or chronic discharge (for example pipeline breakage, tightness loss of a storage means, for example a vat or a tank) or after the shutdown of old industrial sites, a certain amount of hydrocarbon compounds can infiltrate into soils, which leads to the pollution of all or part of said soil, knowledge of the pollutant type (gasoline, kerosene, gas oil, lubricant, chlorine derivatives, etc.) as well as knowledge of the extension in space and in time of the pollution is of great significance for people in charge of diagnosis studies, environmental impact studies and polluted soil rehabilitation. It is in fact well known that the rehabilitation techniques used depend on the type of pollutants.

It is therefore very important to be able to determine quickly the nature of the pollutants and the amount of soil to be treated, that directly depends on the extension of the pollution in depth as well as at the surface. Determination of the degree of pollution of a soil allows to evaluate the volumes of ground to be treated, to determine the best treating methods and thus the costs corresponding to the implementation thereof.

It thus appears that systematic analysis of samples of potentially or really polluted soils allows to make quickly a diagnosis concerning the nature and the extent of the pollution, as well as the main associated risks (contamination of a groundwater table for example).

Knowledge of such information allows to optimize operations of rehabilitation of contaminated sites from the diagnosis stage onwards. Long and costly laboratory analyses, without being completely suppressed, are limited to the necessary minimum amount complementing the information systematically collected by means of the method according to the present invention.

The ROCK-EVAL method developed by the claimant is notably described in documents U.S. Pat. Nos. 4,153,415; 4,229,181; 4,352,673; 4,519,983, as well as French patent application FR-94/08,383. This method, which is fast, practically automatic, has been developed for characterizing mother rocks or reservoir rocks and the hydrocarbons they contain.

However, this method and the device are not suited to characterize precisely the various hydrocarbon cuts that can be contained in soils polluted by such products.

The present invention is thus an improvement on the ROCK-EVAL technique allowing to characterize precisely the pollutants, notably of the hydrocarbon type and/or derivatives (chlorine, sulphur compounds, . . . ), contained in a polluted soil.

SUMMARY OF THE INVENTION

The present invention relates to an improved method allowing fast evaluation of at least one pollution characteristic of natural soils from a sample of said soil, first heated in a non-oxidizing atmosphere, then in an oxidizing atmosphere according to several temperature rise stages. The method comprises at least the stages as follows:

a) the temperature of the sample is quickly raised to a first temperature value $T_1$ ranging between 80 and 120° C. for a determined period $(t_1-t_0)$, b) from the first temperature value, the temperature of the sample is raised to a second temperature value $T_2$ below 200° C. according to a temperature gradient ranging between 2 and 30° C./min, and this temperature $T_2$ is maintained for a determined period $(t_3-t_2)$, c) the temperature is raised from the second value to a third temperature value $T_3$ below 500° C., according to a temperature gradient ranging between 10 and 40° C./min, d) the temperature of the sample is raised from the third value to a fourth value $T_4$ at most equal to 850° C., e) at least four quantities $Q_0$, $Q_1$, $Q_2$, $Q_3$ representative of the nature and of the amount of hydrocarbon compounds contained in said sample are determined from the previous four stages, f) after raising the temperature to the fourth value $T_4$, the residues of said sample are burned in an oxidizing atmosphere from a temperature above 350° C. to a temperature at most equal to 850° C., according to a temperature gradient ranging between 20 and 50° C./min, g) a quantity $Q_4$ representative of the amount of residual organic carbon after the four heating stages is determined, h) at least one pollution characteristic of said sample is deduced from the five quantities $Q_0$, $Q_1$, $Q_2$, $Q_3$ and $Q_4$.

The quantity Q of pollutant can be evaluated according to the formula as follows:

$$Q=Q_0+Q_1+Q_2+Q_3+kQ_4$$

with k ranging from 10 to 11.5.

At least one function relating at least one quantity can be determined from the group made up of $Q_0$, $Q_1$, $Q_2$, $Q_3$ and $Q_4$, and the type "a", "b", "c" or "d" of the pollutant can be distinguished according to at least one specific value of the function for a given sample.

The type "a", "b", "c" or "d" of the pollutant can be distinguished by means of at least one of the specific ratios as follows:

for a pollutant of type "a", the ratio $Q_0/(Q_0+Q_1+Q_2)$ ranges between 0.5 and 1 and the ratio $(Q_3+Q_4)/(Q_0+Q_1+Q_2)$ is close to zero, for a pollutant of type "b", the ratio $Q_0/(Q_0+Q_1+Q_2)$ ranges between 0.05 and 0.5 and the ratio $(Q_3+Q_4)/(Q_0+Q_1+Q_2)$ is close to zero, for a pollutant of type "c", the ratio $Q_0/(Q_0+Q_1+Q_2)$ is close to zero, and the ratio $(Q_3+Q_4)/(Q_0+Q_1+Q_2)$ ranges between 0 and 5, for a pollutant of type "d", the ratio $Q_0/(Q_0+Q_1+Q_2)$ is close to zero, and the ratio $(Q_3+Q_4)/(Q_0+Q_1+Q_2)$ is above 10.

The invention also relates to a device for evaluating at least one pollution characteristic of natural soils contaminated by hydrocarbon compounds, from a sample of said soils placed in a boat, said device comprising a first means for heating said sample in a non-oxidizing atmosphere, means for measuring the amount of hydrocarbon compounds released after feeding the sample into said first heating means, means for transferring the sample into a second heating means in an oxidizing atmosphere, means for measuring the amount of $CO_2$ contained in the effluents discharged from the two heating means, said $CO_2$ measuring means comprising a measuring cell for measuring continuously the $CO_2$ throughout the heating cycle of the first and of the second heating means, and including means for measuring the amount Of $CO_2$ contained in the effluents discharged from the two heating means. The device includes means for determining the pollutant type, for example means for calculating a particular function relating at least one of the Quantities $Q_0$, $Q_1$, $Q_2$, $Q_3$ and $Q_4$.

The device can include means for controlling the temperature of the boats waiting to be fed into said heating means.

The temperature control means can comprise at least one of the following elements: a ventilation, a circulation of a cooling fluid, an insulation.

The boats can include seal means.

The device can comprise means for opening the boats prior to feeding them into the heating means, for example on the loading and transfer arm or on the piston for loading the boat into the oven.

BRIEF DESCRIPTION OF THE DRAWINGS

Other features and advantages of the invention will be clear from reading the description hereafter given by way of non limitative examples, with reference to the accompanying drawings in which.

DESCRIPTION OF THE INVENTION

Figure 1:
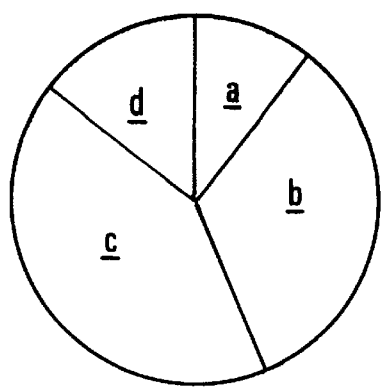
FIG. 1 diagrammatically shows the composition of a soil polluted by various hydrocarbon cuts, FIG. 2 describes the means for implementing the method according to the invention.

FIG. 1 diagrammatically illustrates an example of composition of a natural soil sample contaminated by various types of pollutants.

At least the following four main zones can be distinguished:

zone "a" mainly represents the amount of light hydrocarbon compounds of boiling point below 230° C., such as gasoline, kerosene type cuts and/or light halogenated compounds. In this zone, the number of carbon atoms is mainly below 12. In the present description, the compounds of this zone will be referred to as compounds of type "a";

zone "b" mainly represents the amount of hydrocarbon compounds of boiling point mainly ranging between 230° C. and 400° C., such as "gas oil" type cuts and/or polychlorobiphenyl type halogenated compounds, etc. In this zone, the number of carbon atoms mainly ranges between 13 and 25. In the present description, the compounds of this zone will be referred to as compounds of type zone "c" mainly represents the amount of hydrocarbon compounds of boiling point ranging between 400 and 550° C., such as heavy petroleum cuts, lubricating oils, etc. In this zone, the number of carbon atoms mainly ranges between 25 and 40. In the present description, the compounds of this zone will be referred to as compounds of type "c";

zone "d" mainly represents the amount of hydrocarbon compounds of boiling point substantially above 550° C., such as distillation residues, whose number of carbon atoms is mainly above 40. In the present description, the compounds of this zone will be referred to as compounds of type "d".

Each one of zones a, b, c and d is thus characterised by main compounds in major amount according to the definition above. However, pollutants also containing other compounds of substantially different boiling temperature or of a different number of carbon atoms in relation to what is defined for a given zone may be classified in said zone since they do not modify the characterisation according to the invention.

The object of the method according to the present invention is to allow to distinguish and simultaneously to quantify the various types of pollutants contained in a soil sample in view of their belonging to one of the zones defined above. During a diagnosis survey of a polluted site, soil samples are taken in various places and at various depths in order to be characterised by means of the present method in the corresponding device. The characterisation results allow soil pollution "profiles" to be drawn up by differentiating thus the polluted grounds from the preserved grounds, as well as the nature and the gravity of the pollution.

Figure 2:
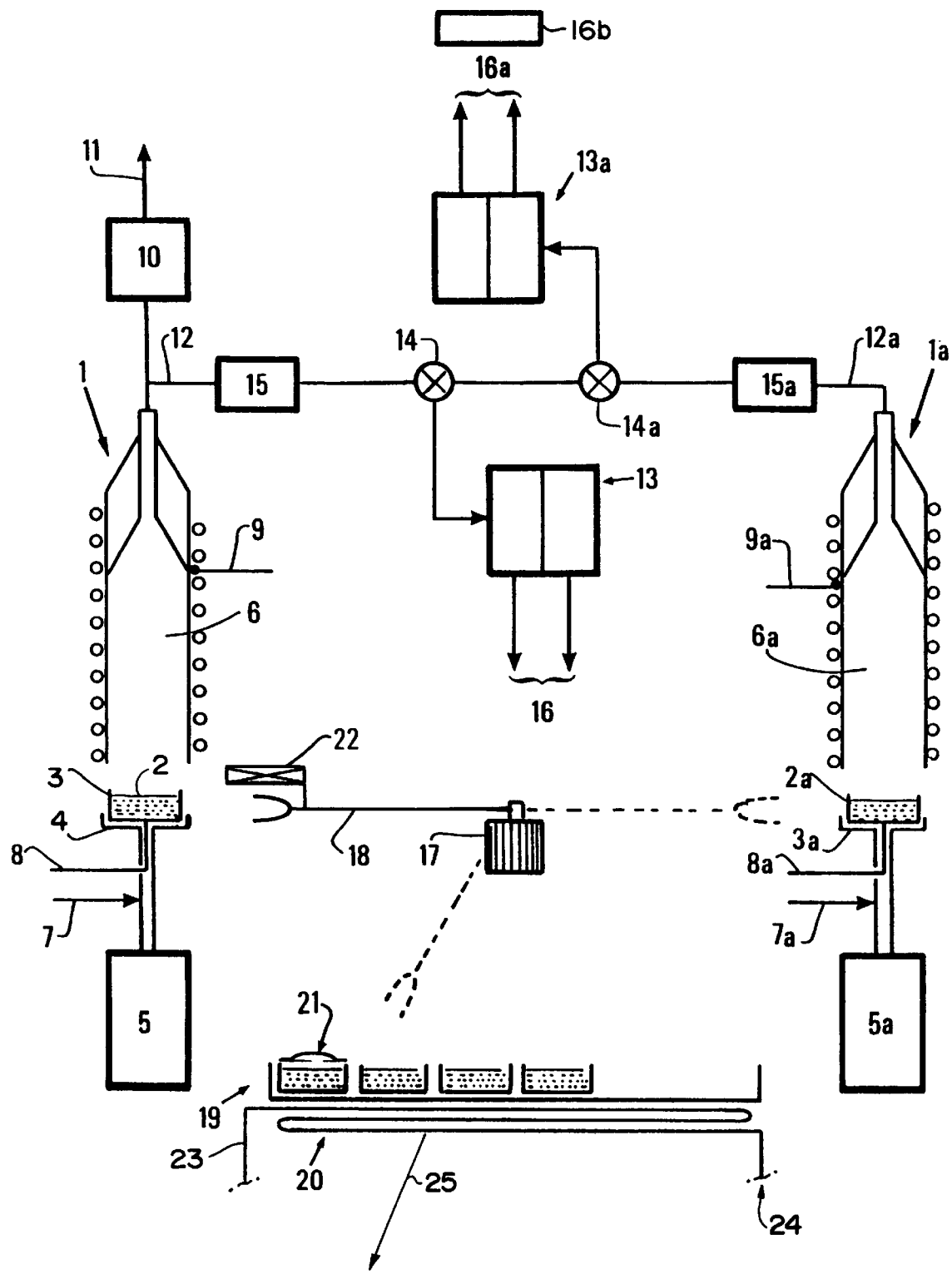

FIG. 2 describes the device allowing the method according to the invention to be implemented. It comprises an automaton that performs the measurements and a PC (personal computer) that controls the automaton, serves as an interface with other computers, manages the analyses, allows real-time visual display of the results and uses control and test softwares.

The measuring device comprises two micro-ovens, a sample changer supplying them with boats and an analysis system consisting of one or several specific detectors, for example a flame ionization detector (FID) or an electron capture detector (ECD), and of infrared cells (IR). These elements are connected to electronics and to a fluid circuit managed by the PC and by the automaton software.

In FIG. 2, reference number 1 shows the heating assembly suited for the pyrolysis of sample 2 placed in a boat 3 borne by a piston 4. Displacement means 5 for moving the boat feed the sample into the inner space 6 of the oven. The displacement means can be pneumatic, hydraulic or electric control jacks. Reference number 7 schematizes the line delivering the carrier fluid for sweeping the products pyrolysed in the oven. This fluid (nitrogen or helium) sweeps the sample by flowing through the piston. Distribution means (not shown) lead the carrier fluid to the upper part of the oven to perform a back-sweeping drain of the inside of the oven when the piston moves back, for example at the end of the pyrolysis process in order to transfer the sample and/or to load another sample. In fact, the influence of oxygen on the organic deposits on the walls of the pyrolysis oven can generate oxygen compounds $CO_2$ and CO that can hinder the analysis.

A temperature probe 8 measures the temperature at the level of the boat bottom, thus very close to the sample. The measuring point of another temperature probe 9 is in the wall of the well, at the level of the upper position of the boat, a position corresponding to the optimum heating point. The temperature programming of the oven is preferably performed by means of probe 8, which allows good control and knowledge of the pyrolysis temperature of the sample.

Temperature probe 9 is used to control the temperature of oven 1 when the oven is open and piston 4 has moved down to extract boat 3 and to replace it by another. The temperature of oven 1 can thus be maintained at a value close to the value determined for the next pyrolysis, which prevents too great a heat loss.

Heating assembly 1a is similar to heating assembly 1 in every respect. This assembly 1a is intended for the operation of oxidation of a sample, generally after pyrolysis. The identical elements bear suffix "a". It may be noted that the fluid injected through line 7a is air in this case.

Heating assemblies 1 and 1a both have temperature regulation means allowing a temperature gradient programming that can reach or even exceed 850° C.

Reference number 10 shows the flame ionization detector FID delivering a signal S representative of the amounts of hydrocarbon products released from the sample during heating. Arrow 11 shows the transfer of signal S to the digitizing means. The flame ionization detector FID must withstand high temperatures, and it therefore requires joints withstanding such conditions without creeping or desorbing products that might cause the base line to drift.

Its linearity and its sensitivity, combined with a very slight base line drift, guarantee high precision in the analysis of hydrocarbons.

The analog signal will be digitized and smoothed with the maximum number of points depending on the programming rate.

An electron capture detector ECD can be used instead of the FID or placed in parallel to another FID type detector, which then requires a distribution means for the flows coming from the oven, for example a pilot valve suited to withstand the high temperatures of the flows.

Line 12 leads part of the flow to means 13 intended for continuous analysis of the amounts of $CO_2$ and of CO produced by pyrolysis of the sample. At the outlet of the pyrolysis oven, the divided flow is heated to at least 360° C. in order to prevent heavy product condensations.

Line 12a leads at least part of the oxidation flow to means 13A intended for continuous analysis of the amounts of $CO_2$ and of CO produced.

Distribution means 14 and 14a allow to use only one or other of the $CO_2$ and CO analysis means for the pyrolysis or oxidation flow. Preferably, for operational time saving reasons, means 13 and 13a will be allocated to only one heating means. The continuous analysis means are for example infrared detectors.

The infrared cells IR, being specific to a gas, can measure continuously the $CO_2$ and CO concentrations in the effluents during pyrolysis and oxidation. They allow to win access to new information such as the presence and the amount of various carbonates, the maximum release temperatures, the peak shapes, the transition between the inorganic carbon and the organic carbon and the distribution of each oxygen compound in the various cracking reactions of the organic matter.

The length of the detector cells depends on the maximum sensitivity required, therefore on the minimum concentration to be measured. It depends on the amounts of $CO_2$ or CO produced by the sample (therefore on its mass), on the analysis time (therefore on the heating conditions) and on the flow rate of the carrier gas that is a diluting factor.

The cell analyzing the $CO_2$ measures maximum concentrations of 2% for a flow rate ranging from 50 to 200 ml. This bracket is linearized on four automatic-change ranges:

range 1: 0 to 2% $CO_2$
range 2: 0 to 1% $CO_2$
range 3: 0 to 0.5% $CO_2$
range 4: 0 to 0.25% $CO_2$ The cell analyzing the CO measures maximum concentrations of 1% under the same conditions as the $CO_2$ cell. The four ranges are:

range 1: 0 to 1% CO
range 2: 0 to 0.5% CO
range 3: 0 to 0.25% CO
range 4: 0 to 0.125% CO.

The signals obtained from cells IR are re-shaped in order to obtain curves with the same attenuation, digitized like the FID signal.

The device also comprises flow purification means 15 and 15a.

Arrows 16 and 16a refer to the transfer of measurements to the electronic digitizing means 16b.

Furthermore, the device includes a sample changer 17 whose arm 18 is suited to shift the boat containing a sample between three possible positions: the pyrolysis oven, the oxidation oven and storage support 19.

The sample changer has simplified mechanics so that displacements can be performed by means of electric stepping motors. Any control possibilities are thus available and they only depend on the working software. For example, it will be possible to load the boats only in the oxidation oven for particular studies. Another possible application will consist in subjecting samples to a heat treatment in an oven and in recovering them afterwards on the boat or storage support 19 in order to analyze them according to the desired cycle.

The boat support is not linear but circular: it exhibits the shape of a carousel, which saves spaces and allows Quicker access to the desired boat by means of a forward or reverse motion of the changer. A number assigned to each location allows passage of the samples to be programmed in the chronological positioning order of the boats on the changer as well as according to either the various cycle or analysis types or to analysis priorities.

The environment of boat support 19 is thermally controlled by thermal regulation means 20 so that the boats waiting to be loaded are maintained at a temperature preventing the start of a vaporization cycle, the boats being on the support. Means (23) 20 can include means of thermal insulation from the heat released by the oven and/or local cooling means, for example a coolant circulation (24), or any other system, e.g., a ventilation element (25).

The boats can comprise caps 21 intended to prevent evaporation of an amount of light pollutant, which might alter the evaluation measurements. In this case, the boats are prepared on the site. The cap has to be perforated prior to feeding the boat into the oven. FIG. 2 diagrammatically shows means 22 connected to the loading arm that can for example strike the cap as the loading arm seizes a boat. Another solution, among others understandable to technicians, can consist in perforating the cap while the boat moves towards or into the oven.

Figure 3:
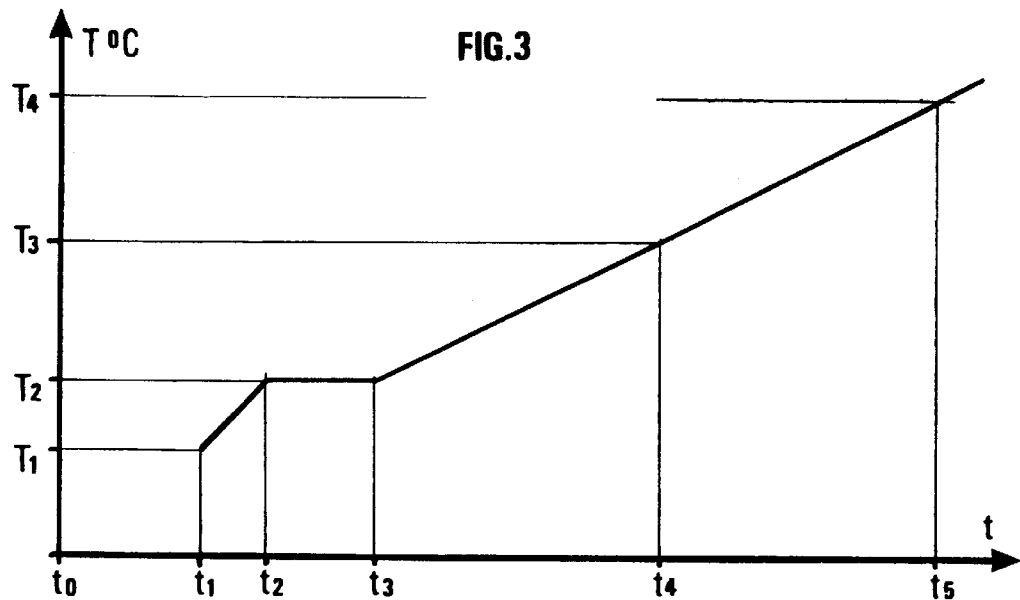
FIG. 3 shows the various sample heating stages as a function of time.

FIG. 3 shows the particular temperature sequences leading to the operation of pyrolysis of a polluted soil sample. There are at least four such temperature sequences. At the time $t_0$, the sample is fed into the oven already heated to the initial temperature $T_1$. This temperature value is below 120° C., preferably close to 80° C. The ascent of the sample in the oven is relatively fast, which allows the sample to be brought very quickly to the internal temperature of the oven. This first heating stage (conventionally called isothermal) lasts for example for a time $t_1-t_0$ of about 10 minutes. From time $t_1$, the temperature of the oven is raised to a temperature $T_2$ below 200° C. and preferably close to 180° C. The temperature rise time $t_2-t_1$ is for example of the order of 5 minutes so as to obtain a temperature gradient ranging between 2 and 30° C./min, but preferably of about 20° C./min. The second heating stage lasts for a time $t_3-t_2$ of about 15 minutes for example. In a programmed pyrolysis stage starting from time $t_3$, the temperature rise is preferably close to 20° C./min up to the temperature $T_3$ corresponding to the time $t_4$. The value of this temperature $T_3$ is about 400° C., preferably close to 370° C. Pyrolysis proceeds until the temperature $T_4$ at most equal to 850° C. is reached. The programmed temperature rise between $t_4$ and $t_5$ is not imposed, the only important factor being the time spent for measurements and the temperature rise capacity of the oven. Temperature $T_4$ can thus be reached with the same temperature gradient as previously between $t_3$ and $t_4$ or with a different temperature gradient.

The pyrolysis residues are thereafter burned in the oxidation oven between 350° C. and 850° C., at a gradient ranging between 25 and 50° C./min, preferably between 35 and 40° C.

Figure 4:
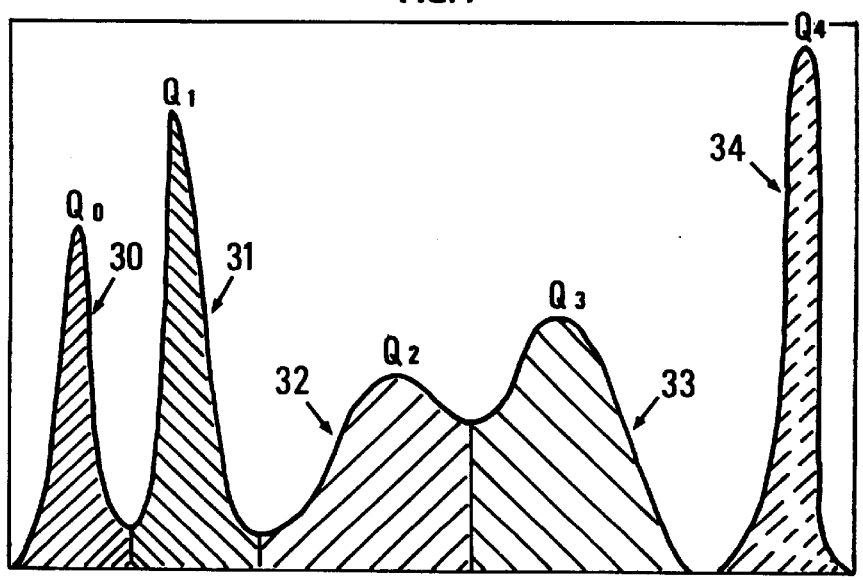
FIG. 4 shows the form of an example of a record of Quantities Q.

FIG. 4 shows quantities representative of all the polluting hydrocarbons that can be contained in a polluted soil according to the composition shown in FIG. 1.

It can be seen that, under the heating conditions described in FIG. 3, the polluted soil sample can give, during a heating program, a first peak $Q_0$, a peak $Q_1$, a peak $Q_2$ and a peak $Q_3$ respectively bearing reference numbers 30, 31, 32 and 33. Peak $Q_4$, bearing reference number 34, corresponds to the stage of oxidation of the pyrolysis residues.

Peaks $Q_0$, $Q_1$, $Q_2$ and $Q_3$ correspond to the release of the hydrocarbon compounds contained in the soil sample in view of the presence of pollutants according to classifications a, b, c and d. It may be reminded that:

type "a" mainly corresponds to the light hydrocarbon compounds whose boiling point is below 230° C., such as gasoline, kerosine type cuts and/or light halogenated compounds. In this zone, the number of carbon atoms is mainly below 12;

type "b" mainly corresponds to the hydrocarbon compounds whose boiling point mainly ranges between 230° C. and 400° C., such as "gas oil" type cuts and/or the polychlorobiphenyl type halogenated compounds, etc. In this zone, the number of carbon atoms mainly ranges between 13 and 25;

type "c" mainly corresponds to the hydrocarbon compounds whose boiling point ranges between 400 and 550° C., such as heavy petroleum cuts, lubricating oils, etc. In this zone, the number of carbon atoms mainly ranges between 25 and 40;

type "d" mainly corresponds to the hydrocarbon compounds whose boiling point is substantially above 550° C. and whose number of carbon atoms is mainly above 40.

Of course, according to the nature of the pollutant or pollutants present in the soil, characterisation may comprise only three, two or even one of these four peaks.

Specifically calibrated calculation means determine the respective amounts of the various pollutant types according to the shape, to the amplitude of said peaks and to the organic carbon remaining after pyrolysis.

In fact, the pyrolysis of heavy products generally involves the formation of coke. The coke is thereafter burned in the second oxidation oven of the device, and the $CO_2$ and the CO produced are measured and summed, which gives a peak representative of a characteristic quantity $Q_4$ (34). The percentage of residual organic carbon in the sample, referred to as residual organic carbon Rc remaining after pyrolysis, as opposed to the pyrolysed organic carbon Pc, is thus determined.

Elementary analyses performed on the coke show that its organic carbon content is 90% on average.

The various quantities $Q_0$, $Q_1$, $Q_2$, $Q_3$ and $Q_4$ are expressed in milligram per gram.

It is from these quantities and from specific ratios between these values that the extent and the nature of the contamination found in the soil can be judged.

It has been determined that certain specific functions of the five quantities $Q_0$, $Q_1$, $Q_2$, $Q_3$ and $Q_4$ allow to define the pollutant types and amounts. In particular, it has been determined that most of the pollutants can be characterised from two functions of the type $f(Q_0, Q_1, Q_2$ and $g(Q_0, Q_1, Q_2, Q_3$ and $Q_4)$.

More precisely: function f can preferably have the form as follows: $Q_0/(Q_0+Q_1+Q_2)$, and g preferably the form as follows: $(Q_3+Q_4)/(Q_0+Q_1+Q_2)$ For a pollutant of type "a", the ratio $Q_0/(Q_0+Q_1+Q_2)$ ranges between 0.5 and 1 and the ratio $(Q_3+Q_4)/(Q_0+Q_1+Q_2)$ is close to zero.

For a pollutant of type "b", the ratio $Q_0/(Q_0+Q_1+Q_2)$ ranges between 0.05 and 0.5 and the ratio $(Q_3+Q_4)/(Q_0+Q_1+Q_2)$ is close to zero.

For a pollutant of type "c", the ratio $Q_0/(Q_0+Q_1+Q_2)$ is close to zero and the ratio $(Q_3+Q_4)/(Q_0+Q_1+Q_2)$ ranges between 0 and 5.

For a pollutant of type "d", the ratio $Q_0/(Q_0+Q_1+Q_2)$ is close to zero and the ratio $(Q_3+Q_4)/(Q_0+Q_1+Q_2)$ is above 10.

FIGS. 5A, 5B, 5C and 5D show four examples of application of the method to soil samples polluted by various hydrocarbon types. Graphs 35, 36, 37 and 38 represent the quantities associated with various polluting hydrocarbons. The pyrolysis program according to FIG. 3 is as follows:

T1=100° C. for 10 minutes;

T2=180° C. (20° C./min gradient);

2-minute isotherm at 180° C.;

T3=370° C. (20° C./min gradient);

T4=850° C. (20° C./min gradient);

oxidation between 350 and 800° C. (35° C./min gradient).

Figure 5C:
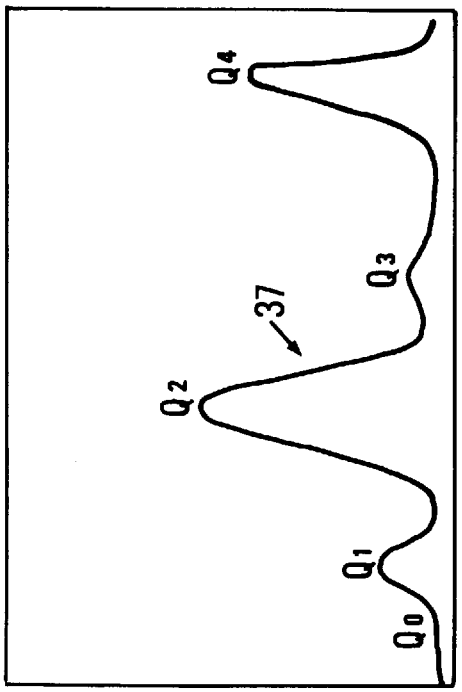
FIGS. 5A, 5B, 5C and 5D illustrate an example of characterisation of the pollutants.
Figure 5D:
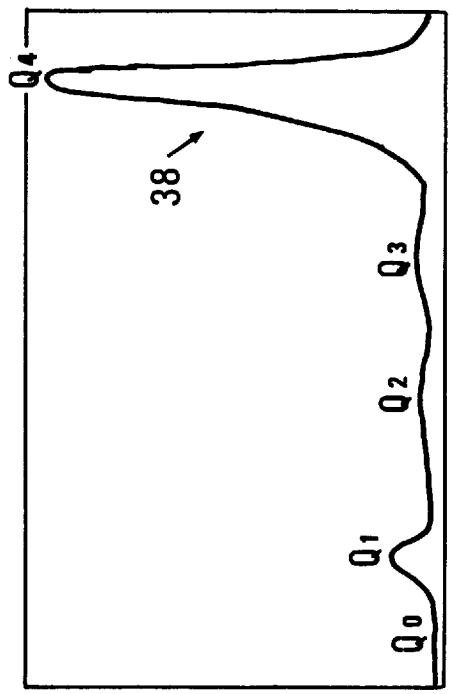
Figure 5A:
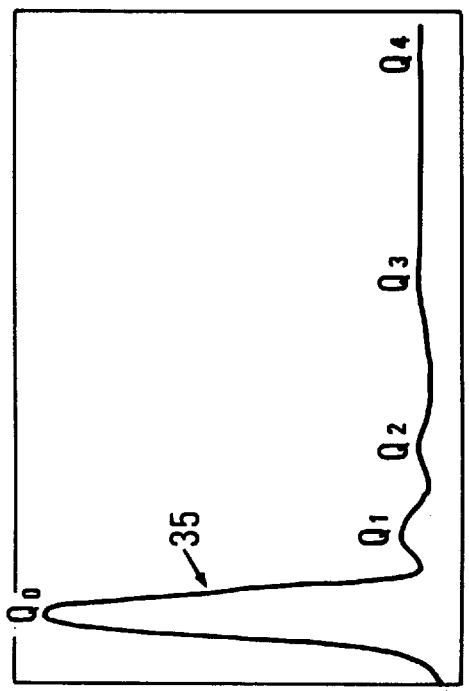

FIG. 5A illustrates a pollution due to a jet fuel, i.e. an aviation fuel belonging to type a. In this example, the ratio $Q_0/(Q_0+Q_1+Q_2)$ is close to 0.86 and the ratio $(Q_3+Q_4)/(Q_0+Q_1+Q_2)$ is close to zero.

Figure 5B:
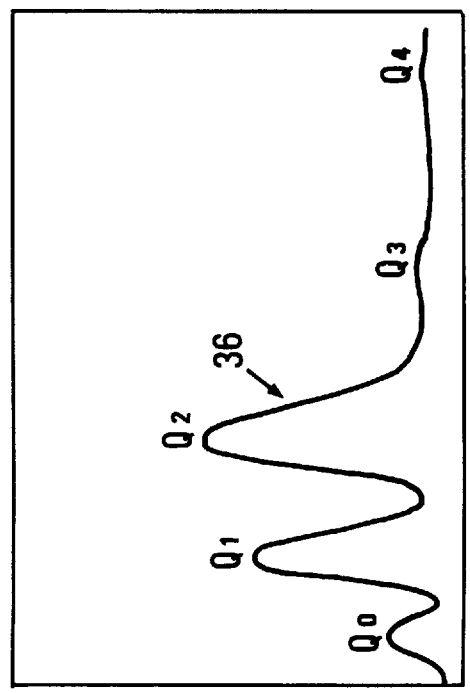

FIG. 5B illustrates a pollution due to an automotive gas oil belonging to type b. In this example, the ratio $Q_0/(Q_0+Q_1+Q_2)$ is close to 0.17 and the ratio $(Q_3+Q_4)/(Q_0+Q_1+Q_2)$ is close to zero.

FIG. 5C illustrates a pollution due to a lubricating oil belonging to type c In this example, the ratio $Q_0/(Q_0+Q_1+Q_2)$ is close to zero and the ratio $(Q_3+Q_4)/(Q_0+Q_1+Q_2)$ is close to 0.4.

FIG. 5D illustrates a pollution due to a coal distillation residue belonging to type d. In this example, the ratio $Q_0/(Q_0+Q_1+Q_2)$ is close to zero and the ratio $(Q_3+Q_4)/(Q_0+Q_1+Q_2)$ is close to 13.

We claim:

1. A device for evaluating at least one pollution characteristic of soil samples contaminated by hydrocarbon compounds, said device comprising a first heater heating a soil sample in a non-oxidizing atmosphere, a measuring device determining an amount of hydrocarbon compounds released after feeding the soil sample into said first heater, a sample transfer device transferring the sample from the first heater into a second heater operating in an oxidizing atmosphere, a $CO_2$ measuring device determining $CO_2$ content of each effluent discharged from said first and second heaters, said $CO_2$ measuring device measuring continuously the $CO_2$ content throughout heating by the first and the second heaters and including a device measuring CO content of each effluent discharged from the two heaters, a temperature controller controlling the temperature of soil samples waiting to be fed into said first heater, and a device determining the pollution characteristic.

2. The device as claimed in claim 1, wherein said temperature controller comprises art least one of a ventilation element, a cooling fluid circulation element or an insulation element.

3. The device according to claim 1, wherein the sample is placed in a boat.

4. The device as claimed in claim 3, wherein the boat comprise a seal.

5. The device as claimed in claim 4, comprising an opener opening the boats prior to feeding them into the first heater.

6. The device according to claim 1, wherein the measuring device determining the amount of hydrocarbon compounds is a flame ionization detector or an electron capture detector.

7. The device according to claim 1, wherein the CO and $CO_2$ measuring devices are at least one infrared detector cell.

* * * * *